(12) United States Patent
Carver

(10) Patent No.: US 11,707,389 B2
(45) Date of Patent: *Jul. 25, 2023

(54) ACROCHORDON EXCISING BANDAGE

(71) Applicant: Tag Off LLC, Wheat Ridge, CO (US)

(72) Inventor: Alan R. Carver, Erie, CO (US)

(73) Assignee: Tag Off LLC, Wheat Ridge, CO (US)

( * ) Notice: Subject to any disclaimer, the term of this patent is extended or adjusted under 35 U.S.C. 154(b) by 34 days.

This patent is subject to a terminal disclaimer.

(21) Appl. No.: 17/208,784

(22) Filed: Mar. 22, 2021

(65) Prior Publication Data

US 2021/0236347 A1 Aug. 5, 2021

Related U.S. Application Data

(63) Continuation of application No. 15/436,799, filed on Feb. 18, 2017, now Pat. No. 10,952,907.

(51) Int. Cl.
| | |
|---|---|
| *A61F 13/00* | (2006.01) |
| *A61F 13/45* | (2006.01) |
| *A61B 17/3205* | (2006.01) |
| *A61F 13/58* | (2006.01) |
| *A61B 17/00* | (2006.01) |
| *A61F 13/15* | (2006.01) |
| *A61F 13/56* | (2006.01) |

(52) U.S. Cl.
CPC .......... *A61F 13/45* (2013.01); *A61B 17/3205* (2013.01); *A61F 13/00063* (2013.01); *A61F 13/58* (2013.01); *A61B 2017/00747* (2013.01); *A61F 2013/00089* (2013.01); *A61F 2013/15008* (2013.01); *A61F 2013/4531* (2013.01); *A61F 2013/4593* (2013.01); *A61F 2013/5666* (2013.01)

(58) Field of Classification Search
CPC .......... A61B 2017/00761; A61B 2017/00774; A61B 2017/00747; A61B 2017/00353; A61B 2017/505; A61B 2017/088; A61B 17/3201; A61B 17/50; A61B 17/3205; A61B 17/326; A61F 2013/00255; A61F 2013/8476; A61F 2013/15032; A61F 2013/1504; A61F 2013/00165; A61F 13/45; A61F 13/58
USPC .......................................................... 602/47
See application file for complete search history.

(56) References Cited

U.S. PATENT DOCUMENTS

| | | | |
|---|---|---|---|
| 2,301,622 | A | 11/1942 | Hambrecht |
| 3,270,745 | A | 9/1966 | Wood |
| 3,358,682 | A | 12/1967 | Preston |

(Continued)

OTHER PUBLICATIONS

U.S. Appl. No. 16/804,931, filed Feb. 28, 2020, Carver.

*Primary Examiner* — Adam Baker
(74) *Attorney, Agent, or Firm* — Craig R. Miles; CR Miles P.C.

(57) ABSTRACT

A bandage system lances a skin tag from a person's body and thereafter projects the wound created. The system has a base layer that is adhesively attached to the person such that the skin tag passes through an opening of the base layer. A cutter is located atop the base layer and uses a pair of blades that are squeezed together to cut the skin tag protruding through the opening. After cutting, a protective layer is adhered to the base layer such that a medicine laden absorbent pad on the protective layer overlays the opening on the base layer absorbing any blood from the wound and applying the medicine to the wound. Thereafter, the system is worn as a typical bandage.

20 Claims, 5 Drawing Sheets

(56) References Cited

U.S. PATENT DOCUMENTS

| | | | |
|---|---|---|---|
| 3,382,873 | A | 5/1968 | Banich et al. |
| 3,760,810 | A | 9/1973 | Van Hoorn |
| 4,226,239 | A | 10/1980 | Polk et al. |
| 4,257,419 | A | 3/1981 | Goltner et al. |
| 4,374,523 | A | 2/1983 | Yoon |
| 4,450,845 | A | 5/1984 | Engel |
| 4,869,268 | A | 9/1989 | Yoon |
| 4,924,864 | A | 5/1990 | Danzig |
| 5,026,379 | A | 6/1991 | Yoon |
| 5,158,563 | A | 10/1992 | Cosman |
| 5,578,047 | A | 11/1996 | Taylor |
| 5,702,356 | A | 12/1997 | Hathman |
| 6,024,742 | A | 2/2000 | Tu et al. |
| 6,241,740 | B1 | 6/2001 | Davis et al. |
| 6,527,786 | B1 | 3/2003 | Davis et al. |
| 7,513,902 | B2 | 4/2009 | Banbury et al. |
| 8,128,637 | B2 | 3/2012 | Sundstrom |
| 8,568,426 | B2 | 10/2013 | Straehnz et al. |
| 9,023,064 | B2 | 5/2015 | Vermeersch |
| RE45,921 | E | 3/2016 | Alferness et al. |
| 10,952,907 | B1 | 3/2021 | Carver |
| 2005/0085751 | A1 | 4/2005 | Daskal et al. |
| 2005/0149063 | A1 | 7/2005 | Young et al. |
| 2005/0277959 | A1 | 12/2005 | Cosgrove et al. |
| 2006/0259042 | A1 | 11/2006 | Ali Hassanien |
| 2006/0282104 | A1 | 12/2006 | Williamson et al. |
| 2007/0276353 | A1 | 11/2007 | Sundstrom |
| 2010/0114131 | A1 | 5/2010 | Rotunda |
| 2011/0218552 | A1 | 9/2011 | Hoffman et al. |
| 2012/0330333 | A1 | 12/2012 | Sundstrom et al. |
| 2013/0123806 | A1 | 5/2013 | Howlett et al. |
| 2013/0150796 | A1 | 6/2013 | Souza et al. |
| 2016/0143654 | A1 | 5/2016 | Zantop |

ACROCHORDON EXCISING BANDAGE

This United States Patent Application is a continuation of U.S. patent application Ser. No. 15/436,799, filed Feb. 18, 2017, now U.S. Pat. No. 10,952,907, issued Mar. 23, 2021, hereby incorporated by reference herein.

BACKGROUND OF THE INVENTION

1. Field of the Invention

The present invention relates to a bandage that is placed at the site of a typical skin tag with a cutting implement resident on the bandage, the cutting implement used to excise the skin tag and thereafter the bandage protects the wound site.

2. Background of the Prior Art

An acrochordon, commonly called a skin tag, is a small benign growth often found in areas where the skin creases, such as the face, especially the eye lids, neck, armpits and groin areas. Skin tags are harmless and normally painless and tend not to grow or change over time. While skin tags of over half an inch in length have been reported, skin tags tend to be about the size of a grain of rice and may have either a smooth or an irregular surface. It is believed that slightly less than half of the population has at least one skin tag.

As skin tags are benign, many people simply ignore them. However, some people desire to have their skin tags removed for cosmetic reasons. For skin tag removal, many people visit a dermatologist or other medical professional with the skin tag removed via excision, cauterization, cryosurgery, or surgical ligation. Skin tag removals are performed in the doctor's office, often with little more than a topical anesthetic placed at the acrochordon site and a bandage placed on the wound site after skin tag removal.

Having a doctor remove a skin tag is a relatively minor procedure, nevertheless, some people do not want to go through the burden or expense of the doctor's visit and opt to remove the skin tag themselves. Using an appropriate cutting implement such as a razor blade, a sharp knife, or eve sufficiently large nail clippers, the person quickly lances the skin tag and simply deals with any pain. While such a home remedy is very quick, it is not without its drawbacks. If the cutting implement is not sterile, a person runs the risk of contracting an infection at the wound site. Some people run the cutting implement under warm water for s short period of time, not realizing that such a procedure may not be sufficient for proper sterilization of the cutting implement. Additionally, if the person misses the mark with the cutting implement, either altogether, or cuts deeper than necessary into the skin, a much larger wound may be created, with the possibility of requiring stitching to close the wound, all with the additional pain created by the additional unneeded cutting. Such misses or deep cuts can be especially problematic when dealing with a skin tag located on an eye lid or otherwise near an eye or other vital organ. Blood splatter can also be a problem.

What is needed is a system that allows for the quick and easy removal of a skin tag from most regions of the body while addressing the above stated shortcomings currently experienced by home acrochordon removal. Specifically, such a device must be sterile so as to help prevent the user from contracting an infection. Such a device must help prevent the person from either missing the skin tag altogether when lancing the skin tagor from cutting too deep into the skin, both to prevent unnecessary pain and damage as well as to prevent possible serious injury to a nearby vital body part. Such a device must help contain any bleeding at the wound site.

SUMMARY OF THE INVENTION

The acrochordon excising bandage of the present invention addresses the aforementioned needs in the art by providing a bandage that a person places at a skin tag site. The bandage has an onboard cutting implement that quickly and easily cuts the skin tag away without missing the skin tag altogether and without cutting too deep into the skin at the skin tag site helping assure of a proper skin tag removal without risk of injury to nearby organs. The acrochordon excising bandage helps contain any blood emanating from the skin tag wound site and helps foster healing of the wound. The acrochordon excising bandage is a one-time sterile device that helps minimize infection risk.

The acrochordon excising bandage of the present invention is comprised of a base layer that has a first upper surface, an adhesive laden first lower surface, and an opening. A cutter is located on the first upper surface and has a first blade that is slidably disposed on a first side of the opening and a second blade that is slidably disposed on an opposing second side of the opening. The first blade and the second blade slide toward and override one another over the opening, thereby cutting a skin tag protruding through the opening and pinched therebetween by the blades. A protective layer has a second upper surface, a second lower surface, and a moisture absorbing pad attached to the second lower surface. The protective layer, connected to the base layer via a flexible neck, is positioned overtop the base layer. In this position, the pad overlays the opening in order to absorb any blood from the wound and otherwise to protect the wound created by the cutter lancing away the skin tag protruding through the opening. The pad is made from a moisture absorbing material such as gauze, water absorbing gel, etc. The pad is medicine laden to help foster quick healing of the wound. The first blade and the second blade are each inwardly arcuate. The first blade has a first nub on a first end thereof and the second blade has a second nub on a second end thereof, the nubs helping in the squeezing operation of the two blades. The first blade is slidably disposed within a first housing attached to the first upper surface of the base layer while the second blade is slidably disposed within a second housing attached to the first upper surface of the base layer. The base layer is made from a flexible material as is the protective layer.

BRIEF DESCRIPTION OF THE DRAWINGS

Similar reference numerals refer to similar parts throughout the several views of the drawings.

DESCRIPTION OF THE PREFERRED EMBODIMENT

Figure 1:
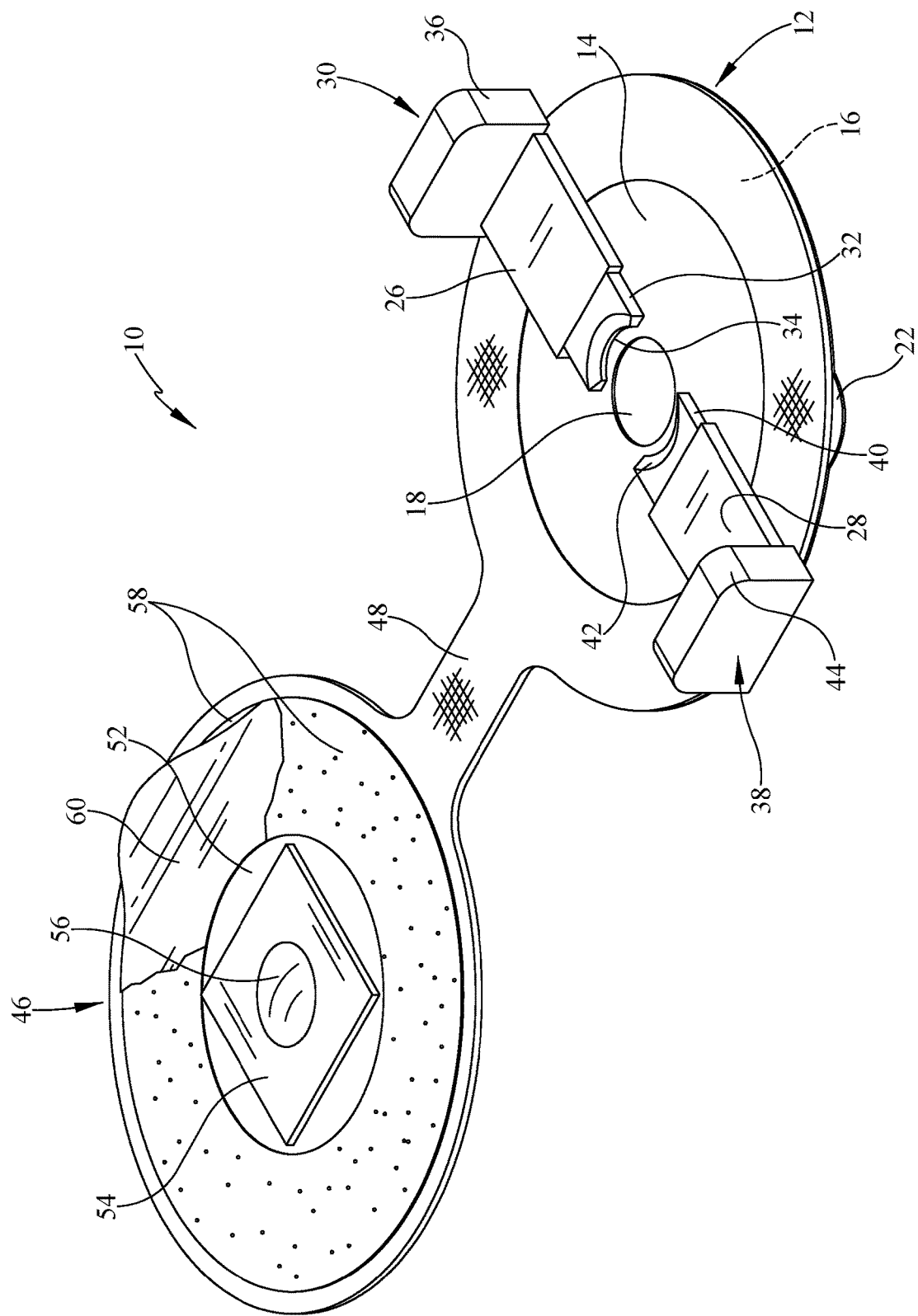
FIG. 1 is a perspective view of the acrochordon excising bandage of the present invention.
Figure 2:
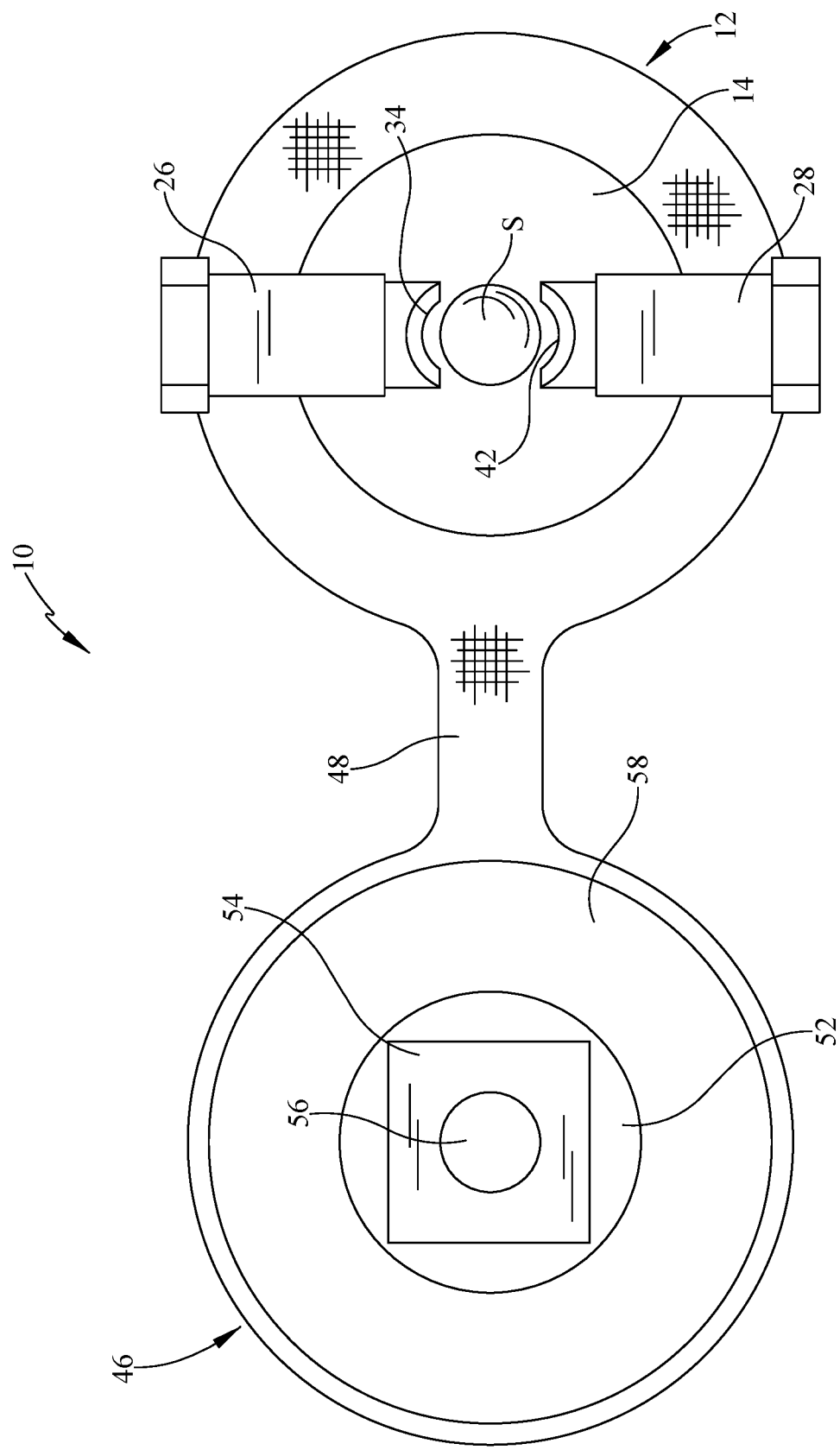
FIG. 2 is a top view of the acrochordon excising bandage.
Figure 3:
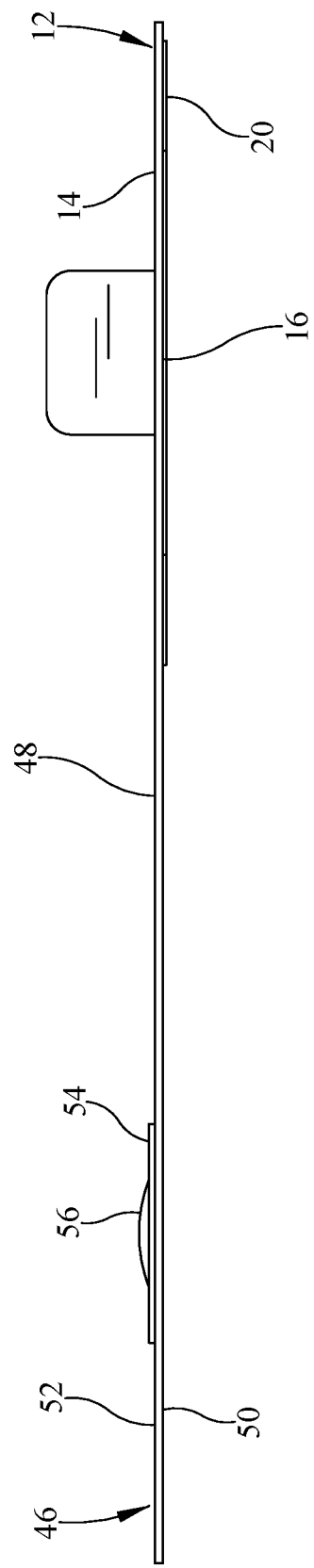
FIG. 3 is a side view of the acrochordon excising bandage

Referring now to the drawings, it is seen that the acrochordon excising bandage of the present invention, generally denoted by reference numeral 10, is comprised of a base layer 12 that has a first upper surface 14, a first lower surface 16, and an opening 18. The base layer 12 is a typical bandage member, an adhesive sheet, and is made from an appropriate bandage material such as woven fabric, plastic (including PVC, polyethylene, and polyurethane) and has an appropriate adhesive 20 located on the first lower surface 16 thereof, the adhesive 20 being made from a bandage appropriate material such as acrylate. The adhesive laden first lower surface 16 of the base layer 12 is protected from exposure prior to use via an appropriate coated first backing layer 22 as is well known in the art.

Figure 4:
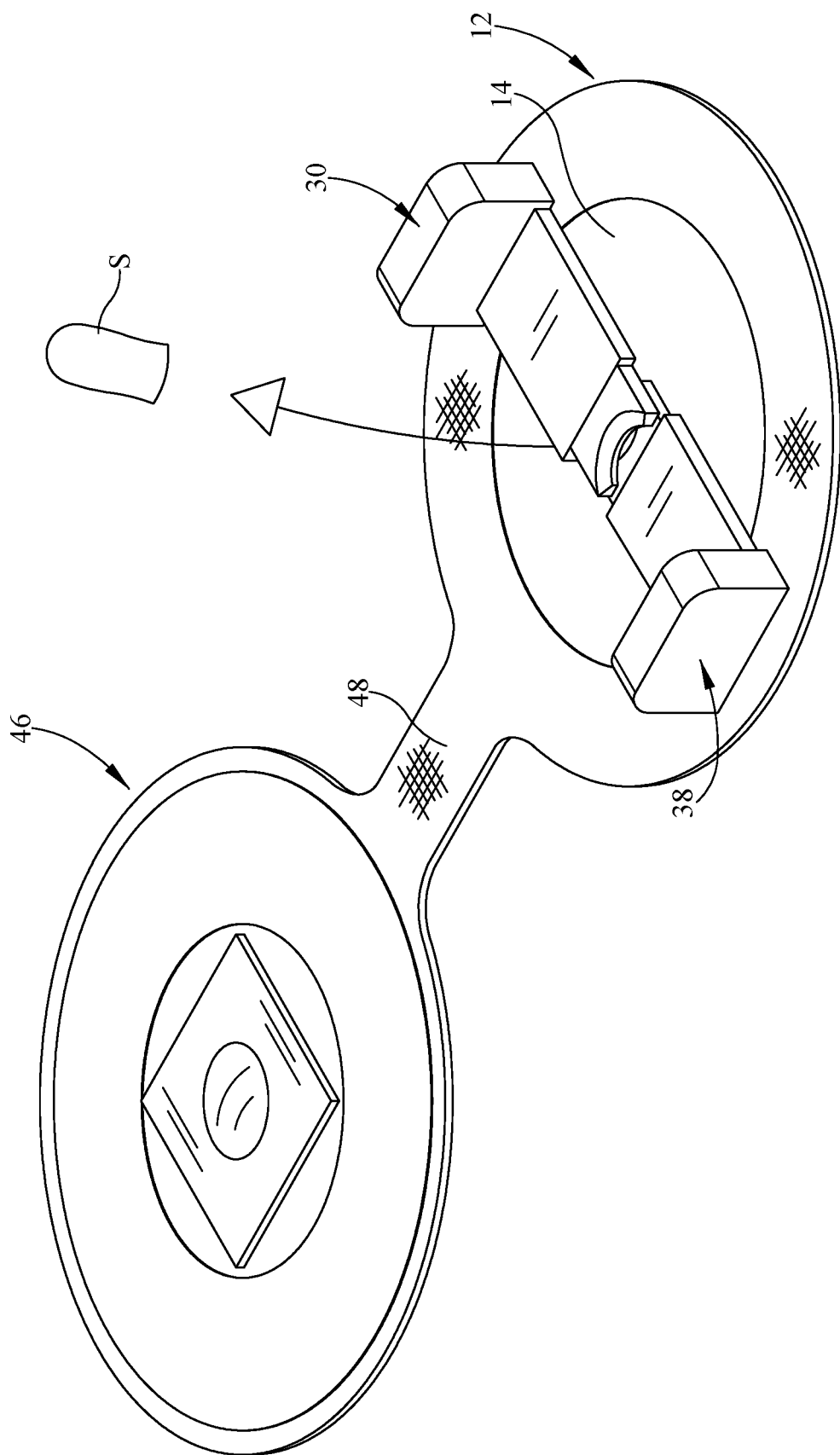
FIG. 4 is an environmental view of the acrochordon excising bandage excising an acrochordon.
Figure 5:
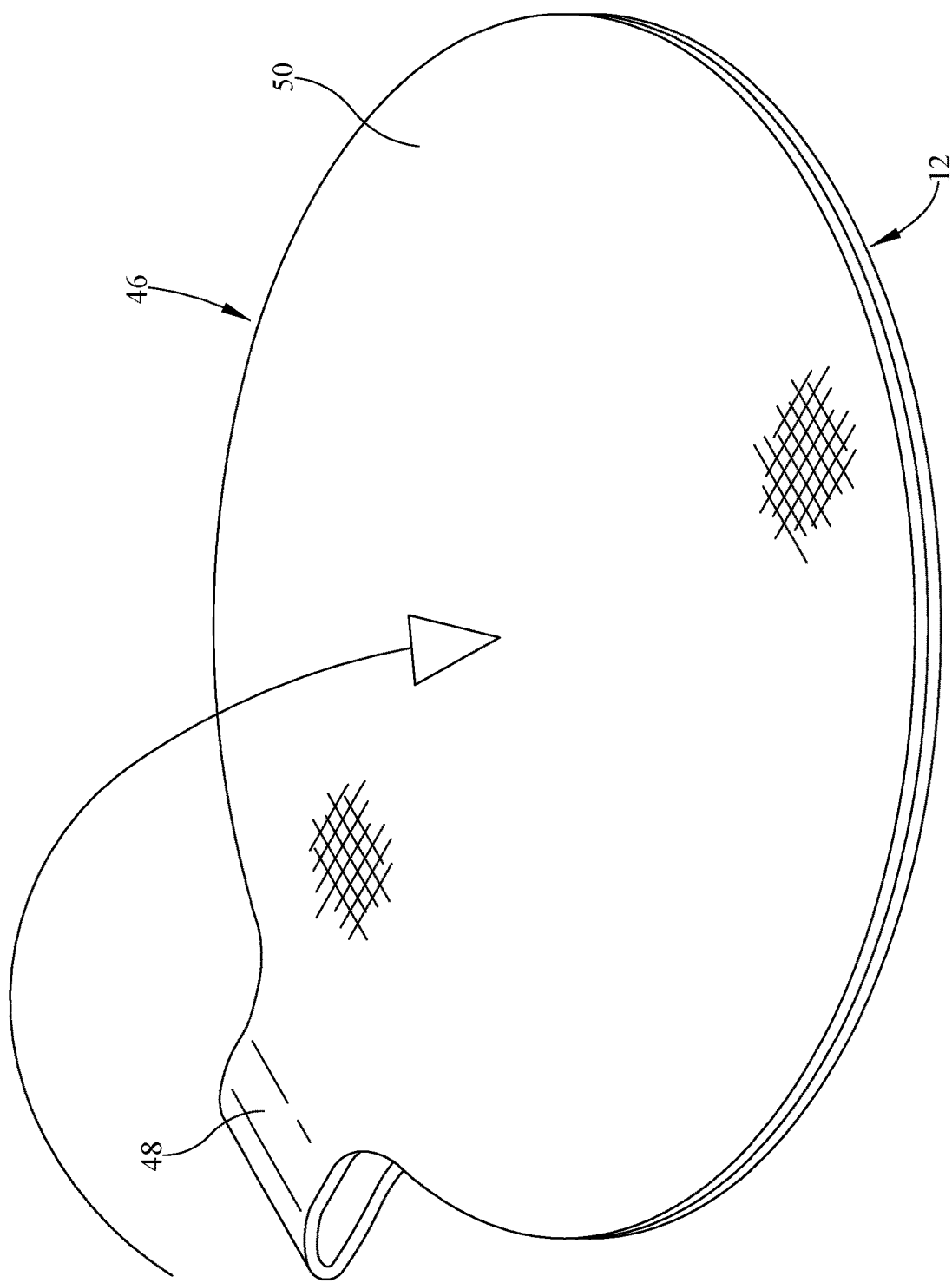
FIG. 5 is a perspective view of the acrochordon excising bandage covering the wound site from where the acrochordon was excised.

A cutting system is located on the first upper surface of the base layer 12. The cutting system is comprised of a first housing 26 attached to the first upper surface 14 on one side of the opening 24 and a second housing 28 attached to the first upper surface 14 on an opposing side of the opening 24, attachment of the first housing 26 and the second housing 28 being in any appropriate manner known in the art, such as via adhesion. A first cutter 30 is slidably disposed within the first housing 26. As seen, the first cutter 30 has a first main body 32 with a first blade 34 (sharpened edge) located on a first end thereof, and a first nub 36 located on a second end thereof. As seen, the first blade 34 may be arcuate. Similarly, a second cutter 38 is slidably disposed within the second housing 28. As seen, the second cutter 38 has a second main body 40 with a second blade 42 (sharpened edge) located on a third end thereof, and a second nub 44 located on a second end thereof. As seen, the second blade 42 may be arcuate. The first main body 32 and the second main body 40 are height offset relative to one another with respect to the base layer 12 so that when the first main body 32 and the second main body 40 are slid toward one another, one of the main bodies 32 or 40 overrides the other main body 40 or 32, as best seen in FIG. 4, so that the first blade 34 and the second blade 42 override one another and thus cut whatever may be therebetween in scissors-like fashion.

A protective layer 46 is connected to the base layer 12 via a neck 48 and has a second upper surface 50 and a second lower surface 52. A pad 54, such as a gauze pad or water absorbing gel or other absorbent pad, is attached to the second lower surface 52 of the protective layer 46 and may have medicine 56 thereon, the medicine 56 being appropriate to foster healing of the wound created as more fully described below and may include a local anesthetic to help numb the pain immediately after wound creation. The outer portion of the second lower surface 52 of the protective layer 44 has an appropriate adhesive 58 located thereon, the adhesive 58 being made from a bandage appropriate material such as acrylate. The protective layer 46 is also a typical bandage member, an adhesive sheet, and is made from an appropriate bandage material such as woven fabric, plastic (including PVC, polyethylene and polyurethane). The neck 48 may also be made from a typical bandage material and the base layer 12, the protective layer 46, and the neck 48 can be made as a single unitary member. The second lower surface 52 is protected from exposure prior to use via an appropriate coated second backing layer 60 as is well known in the art.

The first main body 32 and the second main body 40 are each made from an appropriate material such as stainless steel or hard plastic that can hold a sufficiently sharp edge thereon. The first housing 26 and the second housing 28 can be made from a similar material.

The entire acrochordon excising bandage 10 is held within an appropriate package (not illustrated) in order to keep the acrochordon excising bandage of the present invention 10 sterile prior to use.

In order to use the acrochordon excising bandage 10 of the present invention, the acrochordon excising bandage 10 is removed from its packaging. The first backing layer 22 is removed from the first lower surface 16 of the base layer 12, exposing the adhesive 20 thereon. The base layer 12 is positioned onto a person's body such that the acrochordon S is received through the opening 18 on the base layer 12. The base layer 12 is pressed onto the person's body like any bandage would be placed in order to retain the base layer 12 thereat. Once the base layer 12 is secured on the body, the first main body 32 and the second main body 40 are squeezed toward one another with the assistance of the first nub 36 and the second nub 44, respectively. The squeezing of the first main body 32 and the second main body 40 causes the first blade 34 and the second blade 42 to contact, pinch, and eventually excise the acrochordon S, separating the acrochordon S from the user's body. Thereafter, the first main body 32 and the second main body 40 are retracted, again via the nubs 36 and 44 respectively, in order to expose the opening 18 of the base layer 12 and thus the wound created underneath—the first main body 32 and the second main body 40 may be spring loaded for retraction, but for simplicity of design, such spring loading is not required. Unless the first main body 32 and the second main body 40 have some form of stop system (not illustrated) to help prevent each from being removed from their respective housing 26 and 28, the first main body 32 and the second main body 40 are completely removed from their respective housing 26 and 28 and discarded in appropriate fashion. Thereafter, the second backing layer 60 is removed from the second lower surface 52 of the protective layer 46, and the protective layer 46 is pivoted, via the neck 48, into covering relationship with the base layer 12 so that the protective layer 46 adheres to the base layer 12 via the adhesive 58 located on the second lower surface 52 of the protective layer 46. When the protective layer 46 is properly positioned, the pad 54 and its medicine 56 are positioned over the opening 18 of the base layer 12 and thus the wound created wherefrom the acrochordon S was excised so as to absorb any blood that may have been drawn and to place the medicine 56 onto the wound site. The wound is permitted to heal, protected by the acrochordon excising bandage 10.

While the base layer 12 and the protective layer 46 are illustrated as being generally round, they may have any appropriate shape.

While the invention has been particularly shown and described with reference to an embodiment thereof, it will be appreciated by those skilled in the art that various changes in form and detail may be made without departing from the spirit and scope of the invention.

I claim:

1. A bandage comprising:
   a base layer having a first upper surface, an adhesive-laden first lower surface, and an opening therethrough;
   first and second sharpened edges slidably disposed on said first upper surface on opposing sides of said opening, said first and second sharpened edges configured to excise a skin tag protruding through said opening upon sliding toward and overriding one another over said opening; and
a protective layer coupled to said base layer;
wherein upon overlaying engagement of said protective layer with said base layer, said protective layer disposes over said opening.

2. The bandage of claim 1, wherein said first and second sharpened edges are each arcuate.

3. The bandage of claim 1, wherein said first sharpened edge has a first nub on a first end thereof and said second sharpened edge has a second nub on a second end thereof.

4. The bandage of claim 1, wherein said first sharpened edge is slidably disposed within a first housing attached to said first upper surface of said base layer, and said second sharpened edge is slidably disposed within a second housing attached to said first upper surface of said base layer.

5. The bandage of claim 1, wherein said base layer comprises a flexible material.

6. The bandage of claim 1, wherein said protective layer comprises a flexible material.

7. The bandage of claim 1, wherein said first and second sharpened edges are disposed in vertically spaced-apart relation.

8. The bandage of claim 1, wherein said bandage is sterile.

9. A bandage comprising:
a base layer having a first upper surface, an adhesive-laden first lower surface, and an opening therethrough;
first and second sharpened edges slidably disposed on said first upper surface on opposing sides of said opening, said first and second sharpened edges are height offset relative to one another with respective to said base layer, said first and second sharpened edges configured to excise a skin tag protruding through said opening;
a protective layer coupled to said base layer;
wherein upon overlaying engagement of said protective layer with said base layer, said protective layer disposes over said opening.

10. The bandage of claim 9, wherein said first and second sharpened edges are each arcuate.

11. The bandage of claim 9, wherein said first sharpened edge has a first nub on a first end thereof and said second sharpened edge has a second nub on a second end thereof.

12. The bandage of claim 9, wherein said first sharpened edge is slidably disposed within a first housing attached to said first upper surface of said base layer, and said second sharpened edge is slidably disposed within a second housing attached to said first upper surface of said base layer.

13. The bandage of claim 9, wherein said base layer comprises a flexible material.

14. The bandage of claim 9, wherein said protective layer comprises a flexible material.

15. The bandage of claim 9, wherein upon sliding over said opening, one of said first and second sharpened edges overrides the other of said first and second sharpened edges.

16. The bandage of claim 9, wherein said bandage is sterile.

17. A bandage comprising:
a base layer having a first upper surface, an adhesive-laden first lower surface, and an opening therethrough;
first and second sharpened edges slidably disposed on said first upper surface on opposing sides of said opening;
wherein upon engagement, said first and second sharpened edges separate a skin tag protruding through said opening from a body;
a protective layer coupled to said base layer;
wherein upon overlaying engagement of said protective layer with said base layer, said protective layer disposes over said opening.

18. The bandage of claim 17, wherein said base layer comprises a flexible material.

19. The bandage of claim 17, wherein said protective layer comprises a flexible material.

20. The bandage of claim 17, wherein upon sliding over said opening, one of said first and second sharpened edges overrides the other of said first and second sharpened edges.

* * * * *